United States Patent [19]

Macaulay et al.

[11] Patent Number: 5,160,738
[45] Date of Patent: Nov. 3, 1992

[54] COSMETIC COMPOSITION

[75] Inventors: Ernest W. Macaulay, Bromborough; Richard M. Williams, Caldy, both of England

[73] Assignee: Chesebrough-Pond's U.S.A. Co., Division of Conopco Inc., Greenwich, Conn.

[21] Appl. No.: 727,504

[22] Filed: Jul. 9, 1991

[30] Foreign Application Priority Data

Jul. 9, 1990 [GB] United Kingdom ............ 9015086

[51] Int. Cl.$^5$ .............................................. A61K 7/40
[52] U.S. Cl. ................................ 424/401; 424/61; 424/70; 424/78.03
[58] Field of Search ............ 424/70, 401, 59, 47, 424/78.03, 61; 426/602, 310, 611

[56] References Cited

U.S. PATENT DOCUMENTS

| 4,005,195 | 1/1977 | Jandacek et al. | 514/558 |
| 4,005,196 | 1/1977 | Jandacek et al. | 514/558 |
| 4,034,083 | 7/1977 | Mattson | 514/558 |
| 4,379,755 | 4/1983 | Yamada et al. | 426/602 |
| 4,446,165 | 5/1984 | Roberts | 426/602 |
| 4,822,875 | 4/1989 | McCoy et al. | 426/607 |
| 4,952,687 | 8/1990 | Bodor et al. | 426/611 |
| 4,960,600 | 10/1990 | Kester et al. | 426/310 |

FOREIGN PATENT DOCUMENTS

| 943174 | 12/1963 | United Kingdom . |
| 1587216 | 4/1981 | United Kingdom . |
| 2048670 | 12/1990 | United Kingdom . |

Primary Examiner—Thurman K. Page
Assistant Examiner—D. Colucci
Attorney, Agent, or Firm—Milton L. Honig

[57] ABSTRACT

A cosmetic composition suitable for topical application to human skin or hair comprises a blend of two or more polyol fatty acid polyesters, the polyol having at least 4 free hydroxyl groups, at least 60% of which are then esterified with one or more fatty acids having from 8 to 22 carbon atoms, the composition having a Melting Value of from 20° C. to 60° C., as measured by the Melting Value Test, and preferably a Consistency Value of from 10 to 350, as measured by the Consistency Value Test.

11 Claims, No Drawings

COSMETIC COMPOSITION

FIELD OF INVENTION

The invention relates to cosmetic emollients having occlusive properties when applied to human skin.

BACKGROUND AND PRIOR ART

Hydrocarbons, such as petrolatum (also known as petroleum jelly or soft paraffin) have been used for many years for topical application to human skin for providing an occlusive film thereon to prevent water loss to the environment, thereby promoting hydration by allowing water diffusing from the underlying tissues to accumulate in the stratum corneum. Petrolatum has also been used as an ingredient of skin care products, such as hand creams and lotions, and has also featured in hair grooming or conditioning products, particularly as a setting aid to maintain hair in a desired configuration.

It is, however, widely recognised that petrolatum can impart to the skin and hair an uncomfortable feeling of warmth, in addition to a sticky waxy feel, and this has restricted its use to barrier products such as petrolatum itself or hand creams containing it, where a temporary functional protective film on the skin is desired, and to hair dressings such as pomades.

It is also recognised that petrolatum is derived from fossil fuels, whose supply is non-renewable.

In view of these disadvantages attributable to traditional petrolatum, there exists a need to locate an alternative occlusive product that has all the attributes of emolliency and occlusivity of petrolatum, not only without serious negative subjective properties, but also obtainable from plant-derived sources to suit environmental, ecological and personal health care needs.

SUMMARY OF THE INVENTION

We have now discovered that special polyol fatty acid polyesters, which can for example be derived from natural sugars and vegetable oils, can be employed to provide an ecologically more acceptable emollient product, yet which has the appearance and physical properties of petrolatum.

DEFINITION OF THE INVENTION

Accordingly, the invention provides a cosmetic composition suitable for topical application to human skin or hair, which comprises a blend of two or more polyol fatty acid polyesters, the polyol having at least 4 free hydroxyl groups, at least 60% of which are then esterified with one or more fatty acids having from 8 to 22 carbon atoms, the composition having a Melting Value of from 20° C. to 60° C., as determined by the Melting Value Test. Preferably, the cosmetic composition also has a Consistency Value of from 10 to 350, as determined by the Consistency Value Test.

DISCLOSURE OF THE INVENTION

The cosmetic composition according to the invention comprises a blend of two or more special polyol fatty acid polyesters which are selected for their melting properties and blended in such quantities as to provide a product which has most of the properties of, and advantages attributable to, petrolatum.

The polyol fatty acid polyesters

The composition of the invention comprises a blend of two or more polyol fatty acid polyesters, which are fatty acid polyesters derived from any aliphatic or aromatic polyol which has at least 4 free hydroxyl groups, of which at least 60% of these free hydroxyl groups are then esterified with one or more fatty acids having from 8 to 22 carbon atoms.

It is important that at least 60% of the free hydroxyl groups are esterified, as this renders the polyol fatty acid polyester resistant to cleavage by enzymes, particularly lipase.

The polyol from which the polyol fatty acid polyesters are derived are preferably chosen from sugar polyols, which comprise mono-, di- and polysaccharides.

Preferred examples of monosaccharide sugar polyols include:

Pentose sugar polyols such as D-ribose, D-arabinose, D-xylose, D-lyxose, D-ribulose and D-xylulose.

Hexose sugar polyols such as D-allose, D-altrose, D-glucose, D-mannose, D-gulose, D-idose, D-galactose, D-talose, D-fructose, D-sorbose and D-tagatose.

Heptose sugar polyols, such as D-mannoheptulose and D-sedoheptulose.

The polyol from which the polyol fatty acid polyester is derived can also be chosen from disaccharides such as maltose, lactose, cellobiose, sucrose, trehalose, gentiobiose, melibiose and primeverose.

The polyol from which the polyol fatty acid polyesters are derived can alternatively be chosen from:

tri-saccharides, such as gentianose and raffinose.

The polyol from which the polyol fatty acid polyesters are derived can alternatively be chosen from:

sugar alcohols such as D-mannitol, D-sorbitol, D-ribitol, D-erythritol, D-lactitol and D-xylitol.

The polyol from which the polyol fatty acid polyesters are derived can alternatively be chosen from derivatives of sugars such as α-methyl glucoside and inositol.

The preferred sugar polyol is sucrose.

The fatty acids which are employed to form the polyol fatty acid polyesters of the invention can be individual free fatty acids having from 8 to 22 carbon atoms in the fatty acid molecule.

These fatty acids can be saturated or unsaturated, linear or branched chain fatty acids.

A preferred source of fatty acids for forming the polyol fatty acid polyesters are naturally occurring fats and oils which provide a source of a blend of fatty acids residues, whose choice can vary widely the physical and chemical properties of the polyol fatty acid polyesters obtained therefrom.

These naturally occurring fats and oils can be used as obtained from nature or following full or partial hydrogenation, interesterification, transesterification or fractionation.

Suitable natural sources of these fatty acid residues may be of animal, marine or vegetable origin, such as tallow, lanolin oil, cod liver oil, halibut liver oil, other fish oils, coconut oil, palmkernel oil, palm oil, butter fat, soyabean oil, safflower oil, cotton seed oil, rapeseed oil, poppy seed oil, corn oil, sunflower oil, ground nut oil and mixtures thereof. Preferred fatty acid sources are palm oils, partially hydrogenated palm oils, palmkernel oils, optionally partially hydrogenated soya bean oils and partially hydrogenated fish oils.

By employing a mixture of fatty acids, or one or more naturally occurring oils such as those exemplified above, when synthesising the polyol fatty acid polyester, it is possible to provide polyol fatty acid polyesters in which a mixture of ester groups is present on a single polyol molecule. In this way it is possible to vary the melting characteristics of the polyol fatty acid polyester so formed as desired.

The polyol which can be reacted with a source of fatty acids such as those herein described will, as has previously been stated, comprise at least 4 free hydroxyl groups, any or all of which are available for esterification with the fatty acid moieties. Usually, at least 60% of these free hydroxyl groups are esterified to provide the polyol fatty acid polyester which is to be employed in forming the composition of the invention. More preferably, 70% and ideally at least 80% of these free hydroxyl groups are substituted with fatty acid ester groups.

Selection of polyol fatty acid polyesters according to their individual physical properties i. Melting Characteristics

The selection of the appropriate blend of polyol fatty acid polyesters can be determined by the melting characteristics of each, as conveniently defined by its N-line or N values.

The N-line is the plot of $N_t$—values versus the temperature t. The $N_t$—value is conveniently measured by a nuclear magnetic relaxation technique and is a direct measurement of the level of solid fat content at temperature t. This method is suitably described in Fette, Seifen, Anstrichmittel 80 (5), 180–186 (1978). To some extent, the measurement of $N_t$—values is dependent on the temperature profile used to prepare the samples for the NMR measurement. For the purposes of the invention, the following preparatory temperature profile is adopted: first 30 minutes at 60° C., followed by 90 minutes at 0° C., 4 hours at 20° C., again 90 minutes at 0° C. and finally 60 minutes at the temperature of the measurement, after which the NMR measurement is carried out.

At least one of the polyol fatty acid polyesters, which are used in preparing the composition according to the invention, is characterised by possessing a Melting Value of from −30° to +30° C., and at least one other polyol fatty acid polyester is characterised by possessing a Melting Value of from +30° to +70° C., provided that the difference between the respective Melting Values is at least 5° C., preferably at least 10° C.

It is thus desirable that the composition comprises at least one polyol fatty acid polyester having a low Melting Value and at least one having a high Melting Value, so that the consistency and melting characteristics of the composition itself are suited to topical cosmetic use.

ii. Occlusivity properties

At least one of the polyol fatty acid polyesters, which are used in preparing the composition according to the invention, can also be characterised by possessing an Occlusivity Value of at least 45%, as measured by the Occlusivity Value Test. Preferred polyol fatty acid polyesters are chosen from those which possess an Occlusivity Value of at least 60%, most preferably at least 80% and ideally of at least 80% as measured by this Test. Details of how this test is performed are given later in this specification.

The amount of the polyol fatty acid polyester components to be incorporated in the composition of the invention is up to 100%, i.e. the entire composition can comprise two or more of the polyol fatty acid polyesters as herein defined. It is possible to include other materials in the composition of the invention, examples of which will be given later in this specification, in which case the composition of the invention can comprise from 50% to 99% by weight of polyol fatty acid polyesters.

It is also possible for the composition of the invention comprising essentially a blend of two or more of the special polyol fatty acid polyesters to form a minor or major ingredient of a product suitable for topical application to human skin or hair, in which case such products can comprise up to 50%, preferably from 1% to 30%, and most preferably from 5% to 25% by weight of the blend of special polyol fatty acid polyesters in accordance with the invention.

Physical properties of the composition comprising a mixture of at least two polyol fatty acid polyesters

(i) Melting Value

The composition according to the invention should also have a Melting Value as measured by the Melting Value Test to be described later in this specification of from 20° to 60° C., preferably from 25° to 55° C. Compositions having a Melting Value outside this range are too soft (or even liquid), or too hard for general cosmetic use.

(ii) Consistency Value

The composition according to the invention should also preferably have a Consistency Value of from 10 to 350, most preferably from 15 to 300, as measured by the Consistency Value Test. Compositions having a Consistency Value of less than 10 are generally considered to be too hard for general cosmetic use. Also, compositions having a Consistency Value of greater than 350 are too soft for use where a firm consistency is required.

The method used for measuring the Consistency Value of the composition, is described later in this specification.

(iii) Occlusivity Value

The composition according to the invention should also preferably have an Occlusivity Value of at least 40%, most preferably at least 60% and ideally at least 70%, as measured by the Occlusivity Value Test. Compositions having an Occlusivity Value of less than 40% are unlikely to provide significant protection against water loss from human skin, following topical application thereto, and therefore their ability to promote hydration of stratum corneum is likely to be poor. However, compositions having a low Occlusivity Value can nevertheless find utility in other areas of skin benefit, particularly when employed in a vehicle for the materials whose function is normally to protect skin from adverse environmental hazards, such as excessive exposure to sunlight, or to enhance the condition of skin in other respects.

OTHER INGREDIENTS

The composition according to the invention can optionally comprise other ingredients which can modify the properties attributable to the blend of polyol fatty acid polyesters, as herein defined, or which can be included to provide additional skin or hair benefit properties.

The composition according to the invention can also include sunscreens, healing agents, humectants, thickeners, stabilisers, film formers, emulsifiers, surfactants, preservatives, perfumes, colourants and water.

The composition according to the invention can also comprise other ingredients conventionally used in cosmetic products which are suited to topical application to human skin or hair.

Other ingredients, when present, can form up to 50% by weight of the composition and can conveniently form the balance of the composition.

Process for preparing the composition

The invention also provides a process for the preparation of a composition suitable for topical application to skin or hair, which comprises the step of blending at least two polyol fatty acid polyesters as herein defined.

Use of the composition

The composition according to the invention is intended primarily as a product for topical application to human skin, in particular to form an occlusive layer thereon, to reduce moisture loss. The skin can thereby be protected from adverse climatic conditions, for example from excessive exposure to sun and wind, or from detergent damage, for example that following immersion of the hands in aqueous detergent solution when washing dishes or clothes. A particular use for compositions of the invention is in the manufacture of colour cosmetics, lipsticks and lip salves.

The composition can also act as a carrier for sunscreen agents, perfumes or germicides or other skin benefit agents, whose presence on the skin surface can be prolonged due to the presence of the occlusive film of polyol fatty acid polyesters.

The composition can also be used to treat the hair and the scalp, particularly as a hair hold preparation or grooming aid, to maintain hair in a desired configuration or style.

In use, a small quantity of the composition, for example from 1 to 5 g, is applied to the skin or hair from a suitable container or applicator and, if necessary, it is then spread over and/or rubbed into the skin or hair using the hand or fingers or a suitable spreading device.

Product form and packaging

The composition of the invention can be formulated as a soft solid or jelly-like product having the rheological properties as herein defined, and it can be packaged in a suitable container to suit its viscosity and intended use by the consumer. For example, the composition can be stored in a deformable tube or in a lidded jar.

The invention accordingly also provides a closed container containing the composition as herein defined.

Melting Value Test

As stated earlier, the composition according to the invention should have a Melting Value of from 20° to 60° C., preferably from 25° to 55° C. Also, at least one of the polyol fatty acid polyesters which comprise the composition should ideally possess a Melting Value of from $-30°$ to $+30°$ C., and at least one other polyol fatty acid polyesters should ideally possess a Melting Value of from $+30°$ to $+70°$ C.

The Melting Value of the composition and of the ingredient polyol fatty acid polyesters is measured using a thermometer with a larger than usual bulb.

The procedure for carrying out the Melting Value Test is as follows:

i. melt a small quantity, 20 g is sufficient, of the composition or ingredient polyol fatty acid polyester and heat to a temperature well above its melting point to ensure complete mixing;

ii. allow the melt to cool to a temperature of about 5° C. above its melting point;

iii. immerse a large-bulbed thermometer in iced water to reduce the temperature of the bulb to less than 5° C. and then dip this, after wiping off surface moisture into the melt;

iv. remove the thermometer bulb from the melt and allow the surface of the sample adhering to the bulb to solidify and then place the thermometer once again in iced water to accelerate and ensure complete solidification;

v. place thermometer in a transparent temperature-controlled enclosure and increase heating to raise the temperature at a rate of 2° C. per minute;

vi. observe the bulb of the coated thermometer as the temperature rises until the first drop of the sample falls from the bulb as it melts; the temperature at which this occurs is the approximate Melting Value;

vii. repeat the above procedure using a heating rate, under step v. of 1° C. per minute to obtain a more accurate Melting Value.

The experiment is repeated five times and the mean is then recorded as the Melting Value of the sample.

Consistency Value Test

As stated earlier, the composition of the invention should preferably have a Consistency Value of from 10 to 350, most preferably from 15 to 300 as measured by the Consistency Value Test. The Consistency Value of the composition is accordingly measured by a cone penetrometer, whose construction and use will now be described.

The consistency of the composition of the invention is measured by means of a penetrometer, such as a Model PNR10, supplied by Sommer & Runge KG., Berlin fitted with a polished cone-shaped metal plunger weighing 150 g, having a detachable steel tip of the following dimensions: the tip of the cone has an angle of 30°, the point being truncated to a diameter of $0.381 \pm 0.025$ mm, the base of the tip is $8.38 \pm 0.05$ mm in diameter, and the length of the tip is $14.94 \pm 0.05$ mm. The remaining portion of the cone has an angle of 90° C., is about 28 mm in height, and has a maximum diameter at the base of about 65 mm. The containers for the test are flat-bottomed metal or glass cylinders that are $102 \pm 6$ mm in diameter and not less than 60 mm in height.

The procedure for carrying out the Consistency Value Test is as follows:

Melt a quantity of the composition to be tested at a temperature of $82 \pm 2.5°$ C., pour into one or more containers, filling to within 6 mm of the rim. Cool to $25 \pm 0.5°$ C. over a period of not less than 16 hours, protected from draughts. Two hours before the test, place the containers in a water bath at $25 \pm 0.5°$ C. If the room temperature is below 23.5° C. or above 26.5° C., adjust the temperature of the cone to $25 \pm 0.5°$ C. by placing it in the water bath.

Without disturbing the surface of the composition under test, place the container on the penetrometer table, and lower the cone until the tip just touches the top surface of the test composition at a spot 25 mm to 38 mm from the edge of the container. Adjust the zero setting and quickly release the plunger, then hold it free for 5 seconds. Secure the plunger and read the total penetration from the scale. Make three or more trials, each so spaced that there is no overlapping of the areas of penetration. When the penetration exceeds 20 mm, use a separate container of the test composition for each trial. Read the penetration to the nearest 0.1 mm. Calculate the average of the three or more readings, and conduct further trials to a total of ten if the individual results differ from the average by more than ±3%: the final average of the trials is not less than 1.0 mm and not more than 35.0 mm, indicating a Consistency Value of from 10 to 350.

Occlusivity Value Test

The composition according to the invention can also be characterised by possessing the ability to form an occlusive layer, when applied topically to human skin, so as to reduce the loss of moisture from the skin surface, although this is not essential to the utility of the composition.

Preferably, the composition should have an Occlusivity Value of at least 40%, most preferably at least 50%, as measured by the Occlusivity Value Test.

In view of the wide variation in the characteristics and properties of human skin, as seen amongst a group of individuals of differing ages, races and habitat, it is necessary to provide a standard in vitro test which is readily reproducable, in order to measure the occlusivity of the polyol fatty acid polyester.

An empirical test has accordingly been devised using a standard viscose cellulose film, namely Visking dialysis tubing available from Medicell International Ltd. as a substitute for human skin. This film has a molecular weight cut-off of from 12,000 to 14,000.

In this test, the occlusivity of a film of the composition to the passage of water vapour applied to the dialysis film is measured in a standard manner as follows:

Preparation of occlusivity cell

A 5 ml beaker, for example a Dispo beaker available from American Scientific Products, the diameter of the open end of which is 25 mm (i.e. an area of ~5 cm$^2$), is used to provide an occlusivity cell.

1 ml distilled water is introduced into the beaker and a film of Visking dialysis tubing is stretched across the open end of the beaker and fixed in place with adhesive, for example Assembly Aid Adhesive (3 M).

The rate of water loss through the Visking film at 20° C., at atmospheric pressure and at 50% external relative humidity, is determined by measuring the decrease in weight of the beaker with time using a Sartorius 4503 microbalance, with a D to A converter feeding the output to a chart recorder.

After a steady-state water loss rate has been established, a product whose Occlusivity Value is to be tested, i.e. the composition of the invention comprising at least two polyol fatty acid polyesters, is applied as a film to the surface of the Visking dialysis tubing. When the test substance is liquid or a soft solid, it can be applied using a plastic-gloved finger. When the test material is a solid, it is necessary first to melt it as it is applied to the surface of the Visking dialysis film.

The new steady-state water loss rate, under the same physical conditions of pressure, temperature and relative humidity, is then recorded after excess water from the product has been lost.

Occlusivity of the product film (i.e. the polyol fatty acid polyester) is then calculated as:

$$\% \text{ occlusivity} = 1 - \left[ \frac{\text{water loss rate with product}}{\text{water loss rate without product}} \right] \times 100$$

All water loss rates are corrected for the relatively small rate of water loss through the walls of the beaker (if any). This is determined by measuring the water loss from a beaker where the Visking film is replaced with impermeable aluminium foil.

Occlusivity is normally determined 4 times for each sample. For each measurement, the sample loading is determined from the increase in recorded weight immediately after application to the Visking film of the composition of the invention. Since the loading is not reproducable precisely, a straight line is fitted to a loading versus occlusivity plot (by linear regression) and the occlusivity at a typical consumer product loading of 10 g/sq m is then interpolated.

Experience has shown that about 10 mg of the product applied to the Visking film is sufficient to provide an occlusive layer; without an occlusive layer, the film will normally transmit about 25 g water vapour/m$^2$/hr.

The Occlusivity Value and other physical properties of a series of polyol fatty acid polyesters As has been stated earlier, when selecting polyol fatty acid polyesters for use in preparing the cosmetic composition it is also desirable that at least one of them should also possess an Occlusivity Value of at least 45% preferably at least 60% and ideally at least 80%, as measured by the Occlusivity Value Test.

The Occlusivity Value as measured by the above Occlusivity Value Test of a series of polyol fatty acid polyesters is given in Table 1 below. Included in this table are data relating to other physical properties of these polyesters.

In each case the polyol moiety was sucrose, the fatty acid ester moiety being derived either from specific fatty acids or mixed (unspecified) fatty acid from natural vegetable oils or fats.

TABLE 1

| | | Physical properties of selected sucrose fatty acid polyesters | | | | |
|---|---|---|---|---|---|---|
| Code # | Fatty acid or oil source | Occlusivity Value (%) (+ 2 standard errors) @ 10 gm$^{-2}$ loading | % solids at 30° C. | Melting Value (°C.) | T value [50% solids] (°C.) | Hydroxyl value |
| 1 | palm/palmkernel | 86.8 (6.2) | 35 | 36 | 28 | 2.0 |
| 2 | octatetradecanoic acid | 89.9 (2.3) | 95 | 39 | 36 | 9.6 |
| 3 | soyabean | 93.2 (2.0) | 65 | 50 | 35 | 8.5 |
| 4 | palm/palmkernel | 89.8 (5.1) | 95 | 45 | 36 | 3.8 |
| 5 | soyabean/palm | 86.3 (5.1) | 60 | 43 | 33 | |
| 6 | soyabean | 90.9 (3.6) | 65 | 52 | 38 | 3.3 |
| 7 | soyabean | 94.9 (0.5) | 60 | 45 | 32 | 3.8 |

TABLE 1-continued

Physical properties of selected sucrose fatty acid polyesters

| Code # | Fatty acid or oil source | Occlusivity Value (%) (+ 2 standard errors) @ 10 gm$^{-2}$ loading | % solids at 30° C. | Melting Value (°C.) | T value [50% solids] (°C.) | Hydroxyl value |
|---|---|---|---|---|---|---|
| 8 | palm/palmkernel | 91.5 (2.5) | 70 | 41 | 33 | 1.3 |
| 9 | soyabean | 89.3 (6.2) | 44 | 42 | 28 | 2.6 |
| 10 | palm | 89.2 (1.6) | 14 | 33 | 19 | 5.5 |
| 11 | soyabean | 79.3 (6.8) | 4 | 30 | 16 | 10.5 |
| 12 | soyabean | 11.8 (5.5) | 0 | 10 | <0− | 7.3 |
| 13 | coconut | 47.2 (13.3) | 0 | 24 | 18 | 7.5 |
| 14 | palm | 63.0 (4.5) | 86 | 49 | 40 | 2.4 |
| 15 | fish | 51.2 (4.6) | 98 | 25 | 11 | — |

EXAMPLES

The invention is illustrated with reference to the following examples in accordance with the invention.

EXAMPLES 1 to 4

Examples 1 to 4 illustrate compositions according to the invention consisting of mixtures of two polyol fatty acid polyesters, whose physical properties are given in Table 1.

| | % w/w | | | |
|---|---|---|---|---|
| Example No: | 1 | 2 | 3 | 4 |
| Sucrose Polyester (Code #12) | 40 | 50 | 55 | 60 |
| Sucrose Polyester (Code #8) | 60 | 50 | 45 | 40 |
| Melting Value (°C.) | 39 | 40 | 39 | 41 |
| Consistency Value | 18 | 38 | 58 | 120 |
| Occlusivity Value | 68 | 77 | 52 | 52 |

EXAMPLES 5 to 8

Examples 5 to 8 illustrate compositions according to the invention, each also consisting of mixtures of two polyol fatty acid polyesters, whose physical properties are given Table I.

| | % w/w | | | |
|---|---|---|---|---|
| Example No: | 5 | 6 | 7 | 8 |
| Sucrose polyester (Case #12) | 50 | 60 | 25 | 35 |
| Sucrose polyester (Case #1) | 50 | 40 | — | — |
| Sucrose polyester (Case #10) | — | — | 75 | 65 |
| Melting Value (°C.) | 39 | 40 | 39 | 33.2 |
| Consistency Value | 160 | 180 | 170 | 210 |
| Occlusivity Value | 62 | 67 | 42 | 56 |

EXAMPLES 9 to 12

Examples 9 to 12 illustrate compositions according to the invention consisting of mixtures of more than two polyol fatty acid polyesters, whose physical properties are given in Table I.

| | % w/w | | | |
|---|---|---|---|---|
| Example No: | 9 | 10 | 11 | 12 |
| Sucrose polyester (Code #12) | 14.0 | 20.0 | 25.0 | 40.0 |
| Sucrose polyester (Code #13) | 36.0 | 36.0 | 30.0 | 16.0 |
| Sucrose polyester (Code #11) | 23.0 | 23.0 | 20.0 | 12.0 |
| Sucrose polyester (Code #1) | 13.0 | 13.0 | 13.0 | 20.0 |
| Sucrose polyester (Code #8) | 8.0 | 8.0 | 8.0 | 12.0 |
| Sucrose polyester (Code #4) | 4.0 | — | 4.0 | — |
| Sucrose polyester (Code #14) | 2.0 | | | |
| Melting Value (°C.) | 36.5 | 34.2 | 36.0 | 35.8 |
| Consistency Value: | 136 | 278 | 65 | 120 |

-continued

| | % w/w | | | |
|---|---|---|---|---|
| Example No: | 9 | 10 | 11 | 12 |
| Occlusivity Value: | 62.9 | 54.7 | 59.2 | 57.9 |

EXAMPLES 13 to 16

Examples 13 to 16 illustrate compositions according to the invention which also consists of mixtures of more than two special polyol polyesters, whose physical properties are given in Table I.

| | % w/w | | | |
|---|---|---|---|---|
| Example No: | 13 | 14 | 15 | 16 |
| Sucrose polyester (Code #12) | 14 | 40 | 30 | 40 |
| Sucrose polyester (Code #15) | 36 | 16 | 26 | 16 |
| Sucrose polyester (Code #11) | 23 | 4 | 23 | 12 |
| Sucrose polyester (Code #1) | 13 | 20 | 13 | 20 |
| Sucrose polyester (Code #9) | 8 | 12 | 8 | 12 |
| Sucrose polyester (Code #4) | 4 | 6 | — | — |
| Sucrose polyester (Code #14) | 2 | 2 | — | — |
| Consistency Value: | 17 | 28 | 50 | 28 |
| Melting Value (°C.) | 39 | 39 | 37 | 37 |
| Occlusivity Value: | 73 | 60 | 62 | 68 |

We claim:
1. A cosmetic composition for topical application to human skin or hair consisting essentially of a blend of at least two polyol fatty acid polyesters, wherein a first polyol fatty acid polyester has a Melting Value of from −30° C. to +30° C. and a second polyol fatty acid polyester has a Melting Value of from +30° C. to +70° C., provided that the difference between the respective Melting Values is at least 5° C., the polyesters being formed from esterification between a polyol and at least 1 fatty acid, the polyol having at least 4 free hydroxyl groups, at least 60% of the hydroxyl groups being esterified, the fatty acids having from 8 to 22 carbon atoms, the composition having a Melting Value of from 20° C. to 60° C., as determined by the Melting Value Test.

2. The composition according to claim 1, wherein the difference between the respective Melting Values of the first and second polyol fatty acid polyesters is at least 10° C.

3. The composition according to claim 1, wherein at least one of the polyol fatty acid polyesters has an Occlusivity Value of at least 45%, as measured by the Occlusivity Value Test.

4. The composition according to claim 1, wherein at least one of the polyol fatty acid polyesters is derived from a sugar polyol.

5. The composition according to claim 1, wherein the fatty acid moiety of the polyol fatty acid polyester is derived from one or more oils or one or more fats.

6. The composition according to claim 1, which has a Melting Value of from 25° C. to 55° C.

7. The composition according to claim 1, which has a Consistency Value of from 10 to 350, as measured by Consistency Value Test.

8. The composition according to claim 1, which has an Occlusivity Value of at least 40%, as measured by the Occlusivity Value Test.

9. A method of treating human skin, hair or nails to provide thereon an occlusive layer which comprises the steps of applying topically an effective amount of the composition according to claim 1.

10. A cosmetic composition for topical application to human skin or hair consisting essentially of a blend of at least two polyol fatty acid polyesters, a first polyol fatty acid polyester having a melting value of from −30° C. to +30° C., the polyester being formed by esterification between a polyol and at least one fatty acid derived from a source oil selected from the group consisting of soybean oil, coconut oil and fish oil; a second polyol fatty acid polyester having a melting value of from +30° C. to 70° C., the polyester being formed by esterification between a polyol and at least one fatty acid derived from a source oil selected from the group consisting of palm oil, palm kernel oil and soybean oil, the polyol having at least 4 free hydroxyl groups at least 60% of which are esterified, and the difference between the respective melting values of the polyesters being at least 5° C., and wherein the composition has a Melting Value of from 20° C. to 60° C. as determined by the Melting Value Test.

11. The composition according to claim 10 wherein the first and second polyol fatty acid polyesters are formed by esterification with fatty acids derived from different source oils.

* * * * *